(12) United States Patent
Kim

(10) Patent No.: US 9,081,005 B2
(45) Date of Patent: Jul. 14, 2015

(54) BIOCHIP

(75) Inventor: Sanghyo Kim, Gyeonggi-do (KR)

(73) Assignee: Gachon University Industry University Cooperation Foundation, Gyeonggi-Do (KR)

( * ) Notice: Subject to any disclaimer, the term of this patent is extended or adjusted under 35 U.S.C. 154(b) by 95 days.

(21) Appl. No.: 13/635,060

(22) PCT Filed: Mar. 18, 2011

(86) PCT No.: PCT/KR2011/001878
§ 371 (c)(1),
(2), (4) Date: Sep. 14, 2012

(87) PCT Pub. No.: WO2011/115445
PCT Pub. Date: Sep. 22, 2011

(65) Prior Publication Data
US 2013/0011914 A1    Jan. 10, 2013

(30) Foreign Application Priority Data

Mar. 19, 2010 (KR) .................. 10-2010-0024646
Mar. 17, 2011 (KR) .................. 10-2011-0023941

(51) Int. Cl.
*B82Y 30/00* (2011.01)
*G01N 33/543* (2006.01)

(52) U.S. Cl.
CPC .......... *G01N 33/54373* (2013.01); *B82Y 30/00* (2013.01)

(58) Field of Classification Search
None
See application file for complete search history.

(56) References Cited

U.S. PATENT DOCUMENTS

| 5,866,433 | A | * | 2/1999 | Schalkhammer et al. | ..... 436/525 |
| 6,040,191 | A | * | 3/2000 | Grow | .............. 506/12 |
| 2004/0189311 | A1 | * | 9/2004 | Glezer et al. | .................. 324/444 |
| 2009/0325812 | A1 | * | 12/2009 | Mirkin et al. | ..................... 506/8 |

FOREIGN PATENT DOCUMENTS

| JP | 10267841 A | 10/1998 |
| JP | 2005291966 A | 10/2005 |
| KR | 20100002960 A | 1/2010 |
| KR | 20100043432 A | 4/2010 |

OTHER PUBLICATIONS

Herr, "Microarrays: Preparation, Microfluidics, Detection Methods, and Biological Applications," K. Dill et al, ed., Chapter 8, pp. 169-190 (2009).*
Wang, Yijin et al., "A CMOS Image Sensor utilizing Opacity of nanometallic Particles for DNA Detection", Electron Devices, IEEE Transactions, vol. 54 Issue 6 (Jun. 2007), pp. 1549-1554. Abstract Only.

(Continued)

*Primary Examiner* — Robert T Crow
(74) *Attorney, Agent, or Firm* — Faegre Baker Daniels LLP

(57) ABSTRACT

A biochip including a metal nanoparticle layer on a multi-layer substrate can perform qualitative and quantitative analyses simply without a separate tag. A biochip including a metal nanoparticle layer on a multilayer substrate and using a CMOS image sensor can be an economically beneficial biochip reusable and convenient in use by employing a relatively simple detection method without a need of using a separate tag.

4 Claims, 6 Drawing Sheets

(56) References Cited

OTHER PUBLICATIONS

Yang, Yaemoon et al., "In Situ Detection of Live Cancer Cells by Using Bioprobes Based on Au Nanoparticles", Langmuir, vol. 24, No. 21 (2008), pp. 12112-12115.

Glaever, Ivar et al., "A New Assay for Rheumatoid Factor", Clinical Chemistry, vol. 30, No. 6, (1984) pp. 880-883.

International Search Report and Written Opinion issued in PCT/KR2011/001878, mailed Nov. 30, 2011, 14 pages. (English Translation Attached).

\* cited by examiner

BIOCHIP

This application is a national phase application of PCT application PCT/KR2011/001878filed pursuant to 35 U.S.C. §371, which claims priority to Korean Patent Application No. 10-2011-0023941, filed Mar. 17, 2011 and Korean Patent Application No. 10-2010-0024646, filed Mar. 19, 2010, which are incorporated herein by reference in their entirety for all purposes.

BACKGROUND OF THE INVENTION

1. Field of the Invention

The present invention relates to a biochip capable of performing qualitative and quantitative analyses simply without a separate tag by including a metal nanoparticle layer on a multilayer substrate.

2. Background Art

A biochip is a hybrid device made in the form of an existing semiconductor chip by combining bio-organic matters derived from living creatures, such as enzymes, proteins, antibodies, DNA, microorganisms, animal or plant cells, organs, neurons, etc., with inorganic matters, such as semiconductors or glass. Using inherent functions of biomolecules and mimicking functions of organisms, the biochip diagnoses infectious diseases or analyzes genes and thus can be used as a new functional device for processing information.

Depending on the biological substances and the degree of systemization, the biochip is classified into a DNA chip, an RNA chip, a protein chip, a cell chip, a neuron chip, etc. In a broad definition, the biochip can also include a biosensor capable of detecting and analyzing a variety of biochemical substances, such as a lab-on-a-chip (LOC) that integrates having automatic analyzing functions, including pretreatment of samples, biochemical reaction, detection, and data analysis.

The biochip-based analysis involves labeling a sample with a tag such as a fluorescent substance and applying an excited radiation to the sample to measure the emission wavelength and intensity. The analysis system using a fluorescent substance is, however, extremely complicated in detection method, requiring expensive equipment for analysis at high cost and entailing difficulty of long-term measurement due to low luminous efficiency and relatively short life span of fluorescent bodies.

SUMMARY OF THE INVENTION

It is therefore an object of the present invention to provide a biochip reusable and convenient in use by employing a relatively simple detection method without a need of using a separate tag in qualitative and quantitative analysis of a biological substance.

To achieve the object of the present invention, the present invention is to provide a biochip including: a multilayer including a substrate, a metal nanoparticle layer deposited on the substrate, and a dielectric layer deposited on the metal nanoparticle layer in each substrate; and a CMOS image sensor.

The present invention is also to provide a biochip including: a multilayer substrate, a metal nanoparticle layer deposited on the substrate, a dielectric layer deposited on the metal nanoparticle layer in each substrate, and a charging layer deposited on the metal nanoparticle layer deprived of the dielectric layer; and a CMOS image sensor.

The biochip of the present invention including a metal nanoparticle layer on a substrate and using a CMOS image sensor can be an economically beneficial biochip reusable and convenient in use by employing a relatively simple detection method without a need of using a separate tag.

DETAILED DESCRIPTION OF THE PREFERRED EMBODIMENT

Figure 1:
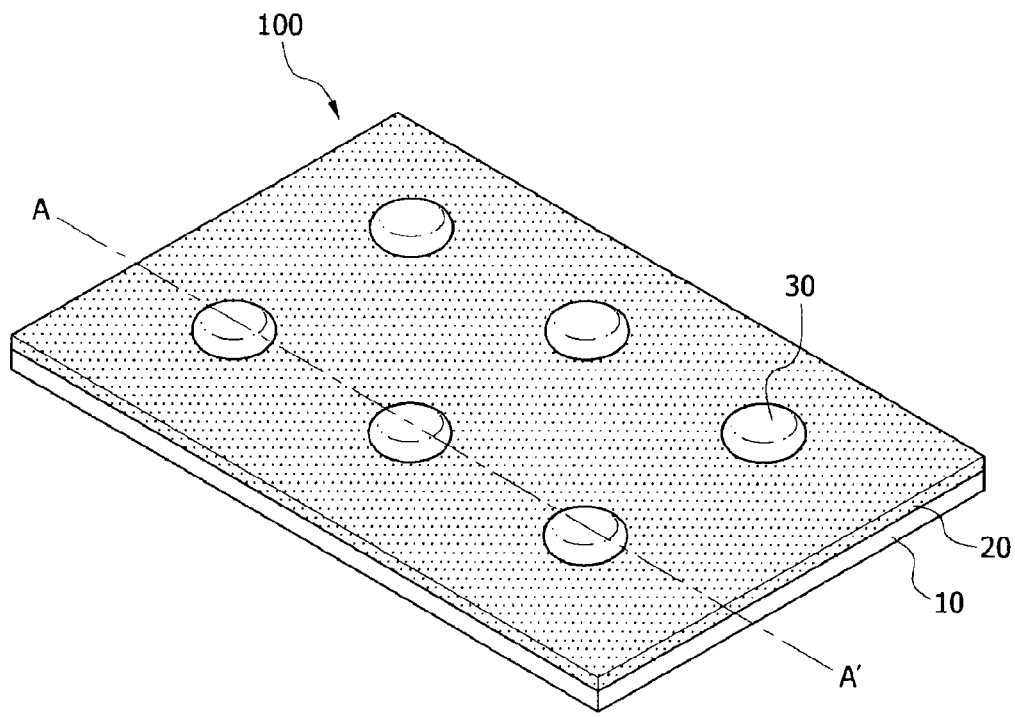
FIG. 1 is a diagram showing the structure of a multilayer according to one embodiment of the present invention.

The present invention provides a biochip including: a multilayer including a substrate, a metal nanoparticle layer deposited on the substrate, and a dielectric layer deposited on the metal nanoparticle layer in each substrate; and a CMOS image sensor.

In the present invention, the multilayer substrate may consist of layer separated from one another by separate partitions, or a dielectric layer separately deposited on a metal nanoparticle layer corresponding to each layer without using separate partitions.

Including a metal nanoparticle layer deposited on a multilayer substrate, the biochip according to the embodiments of the present invention can measure the change in the intensity of light based on the change of light scattering in each layer bound to a biological substance using interactions between the biological substances without a need of using a separate tag, as in the indium slide immunoassay (ISI) method, thereby easily analyzing the type and quantity of the biological substance undergoing analysis. In other words, the biological substance binds to the metal nanoparticle layer to block photons penetrating into the CMOS image sensor and reduce the number of photons absorbed by the CMOS lens, reducing the intensity of light, and the measurement of such a change in the intensity of light enables a quantitative analysis. Hence, the present invention is advantageously capable of using a visible light source to perform qualitative and quantitative analyses of a biological substance with ease.

The present invention, which includes a CMOS image sensor (CIS) as a sensor for detecting a light signal generated from the substrate and converting it into a digital electronic signal, can realize a driving system using convenient and various scanning methods and integrate a signal processing circuit in a single chip to facilitate device minimization. Further, the present invention can alternatively use CMOS techniques, reducing the production cost with extremely low power consumption, which makes it possible to apply to products with limited battery capacity.

The principle of CMOS image sensors can be described in summary as follows. A single light diode provided in the sensor is in charge of absorption of light and conversion of light into a different signal, which follows the photoelectric effect. As photons are accumulated in the form of electric charges and converted from electrons, the quantity of photons is in proportion to the number of electric charges detected in contact with the CMOS image sensor. The electric charges are amplified into an analog voltage, which is converted into a digital number. The digital number displayed as a digital output is proportionate to the number of photons detected by the CMOS image sensor. If any, another material sticking on the surface of the CMOS image sensor may interfere with the passage of photons reducing the digital output number.

In the present invention, production of a biochip by combining a multilayer substrate and a CMOS image sensor together can be carried out according to any known method which can be appropriately selected by those skilled in the art. For example, a multilayer substrate and a CMOS image sensor are prepared separately in a different substrate by a separate process and then packaged together into a single biochip. More specifically, if not specifically limited, a multilayer substrate and a CMOS image sensor can be formed by a different fabrication process and packaged into a single biochip.

The substrate used is not specifically limited and may be any kind of substrate commonly used for biochips, including glass substrate, silicon substrate, plastic substrate, compound semiconductor substrate, quartz substrate, sapphire substrate, etc.

In one embodiment of the present invention, the metal nanoparticle layer deposited on the substrate may be an indium or gold nanoparticle layer. But, the metal nanoparticle layer is not specifically limited to an indium or gold nanoparticle layer and may include any kind of metal nanoparticle layer known in the related art.

The size of the metal nanoparticle may be dependent upon the type of the biological substance used as a dielectric and range from several nanometers to several hundred nanometers. This is because that the metal nanoparticles after binding to a biological substance become larger than the wavelength of the visible light due to the size of the biological substance and turn to opaque.

In the following examples, the size of the metal nanoparticles and the thickness of the metal nanoparticle layer deposited on the substrate affected the binding efficiency of the biological substance, thereby changing the sensitivity of the CMOS image sensor. In other words, a measurement of signals generated by a binding of primary and secondary antibodies using a gamma-interferon dielectric showed that the antibody binding efficiency was high to achieve high sensitivity when the metal nanoparticle layer was 10 or 20 nm in thickness, with the diameter of metal nanoparticles in the range of 70 to 100 nm or 150 to 200 nm.

Therefore, according to one embodiment of the present invention, the size of the metal nanoparticles may be 60 to 300 nm, 60 to 250 nm, 70 to 250 nm, or 70 to 200 nm.

In accordance with another embodiment of the present invention, the thickness of the metal nanoparticle layer may be 50 to 30 nm, 5 to 25 nm, 7 to 30 nm, 7 to 25 nm, 9 to 30 nm, or 9 to 65 nm.

When a metal, such as indium or gold, evaporates on a substrate under vacuum, metal atoms coagulate as minute particles on the substrate. Here, the size of the metal particles can be determined depending on the quantity of the evaporated metal or the temperature of the medium.

The deposition of metal nanoparticles can be carried out by a known method in the related art, including, if not specifically limited to, a method disclosed in "Giaever et al., *A New Assay for Rheumatoid Factor, Clinical Chemistry*, Vol. 30, No. 6, 1984", where indium (Indium corp. of America, Utica, N.Y. 13503) is deposited into nanoparticles under a reduced pressure of $10^{-6}$ mmHg on the glass substrate of a reduced-pressure evaporator. If not specifically limited to, a metal can be deposited into metal particles having a diameter of several score nanometers to several hundred nanometers at 350 to 700° C., under a reduced pressure of $10^{-8}$ to $10^{-4}$ mmHg for about 1 to 10 minutes.

In still another embodiment of the present invention, the dielectric layer deposited on the metal nanoparticle layer in each substrate may include a biological substance selected from the group consisting of DNA, RNA, protein, enzyme, antigen, antibody, peptide, carbohydrate, and lipid. For example, an antigen protein that specifically binds to an antibody protein undergoing analysis is used as a probe protein to form a dielectric layer on the metal nanoparticle layer in each cell substrate.

Deposition of a different biological substance in each layer enables not only qualitative analysis of an analyte specifically binding to each biological substance but also quantitative analysis of the analyte by measuring the light signal from each reaction substrate. The substance that can be analyzed using the biochip of the present invention is any substance specifically binding to the biological substance used as a dielectric layer, such as being selected from the group consisting of DNA, RNA, protein, enzyme, antigen, antibody, peptide, carbohydrate, and lipid.

A solution containing a biological substance is used to deposit the biological substance on a slide. The slide is washed and dried out to remain the biological substance deposited as a single layer on the metal nanoparticle layer. The biological substance thus deposited acts as a dielectric layer. When the metal nanoparticle layer is covered with a dielectric layer, light scattering by the metal nanoparticles increases to vary the intensity of the light, allowing a qualitative analysis of the portion with the dielectric layer on.

In still another embodiment of the present invention, the multilayer substrate may further include a charging layer deposited on the metal nanoparticle layer deprived of the dielectric layer. In other words, a separate charging layer is deposited on a remainder of the metal nanoparticle layer not covered with the dielectric layer to produce a biochip, which includes: a multilayer substrate, a metal nanoparticle layer deposited on the substrate, a dielectric layer deposited on the metal nanoparticle layer in each substrate, and a charging layer deposited on the metal nanoparticle layer deprived of the dielectric layer; and a CMOS image sensor. The charging layer may not be deposited on the dielectric layer but on the metal nanoparticle layer as a single layer. In other words, an inert protein that does not bind to a biological substance corresponding to the dielectric layer is deposited on the remainder surface of the substrate other than the dielectric layer, making the surface of the substrate uniform.

According to one embodiment of the present invention, the charging layer includes, but is not limited to, a metalloprotein. The term "metalloprotein" as used herein refers to a protein composite binding to a metal ion, such as iron, copper, zinc, etc.

In accordance with one embodiment of the present invention, the metalloprotein includes, but is not limited to, aldolase.

The sample is put on the multilayer substrate having a uniform surface characteristic to analyze the biological substance qualitatively and quantitatively. For example, when an antibody protein contained in the sample undergoing analysis binds specifically to an antigen protein in a specific layer of a specific biochip by way of antigen-antibody reaction, the corresponding portion has a change of light scattering and becomes distinguished qualitatively from the other portion where no change of light scattering occurs, thereby allowing a qualitative analysis to determine the type of the antibody protein in the sample. Furthermore, the intensity of light transmitted through the multilayer substrate decreases with an increase in the quantity of the binding protein, so the binding protein can be quantitatively determined by measuring the change of the intensity of the transmitted light using a CMOS image sensor or by carrying out visual inspection.

The biochip of the present invention can be reused by washing the surface of the multilayer substrate to take the antibody protein binding to the probe protein off the substrate after the protein analysis.

Hereinafter, the present invention will be described in further detail with reference to the accompanying drawings, which are given only for the specific description of the present invention and not intended to limit the scope of the present invention.

FIG. 1 is a diagram showing the structure of a multilayer substrate according to one embodiment of the present invention.

The multilayer substrate 100 of the present invention includes a substrate 10, a metal nanoparticle layer 20 deposited on the substrate, and a dielectric layer 30 deposited on the metal nanoparticle layer in each substrate.

In FIG. 1, the multilayer substrate is not divided into layers by separate partitions, but the dielectric layer 30 is deposited at a portion corresponding to each layer to form the multilayer substrate 100. Alternatively, the multilayer substrate can be divided into layers by separate partitioned.

Figure 2:
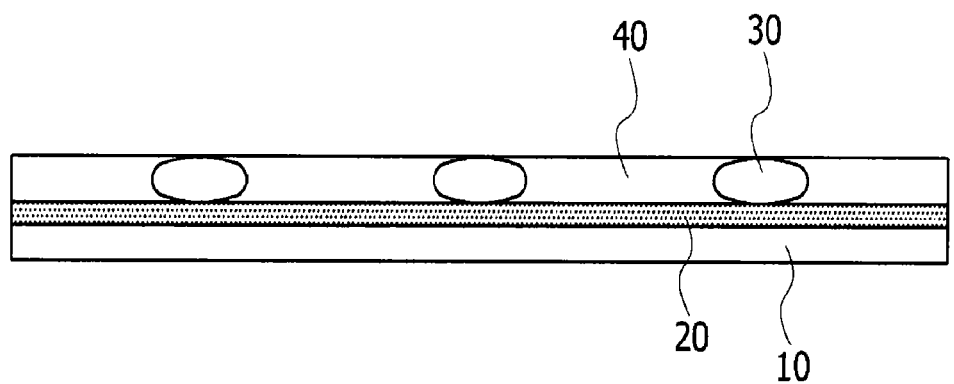
FIG. 2 is a cross section taken by A-A' of FIG. 1.

FIG. 2 shows a cross-sectional structure of the multilayer substrate taken by A-A' of FIG. 1. The multilayer substrate further includes a charging layer 40 deposited on the metal nanoparticle layer 20 deprived of the dielectric layer 30. The multilayer substrate shown in FIG. 2 includes the dielectric layer 30 and the charging layer 40 deposited as a single layer on the metal nanoparticle layer 20, forming a uniform surface layer.

Figure 3:
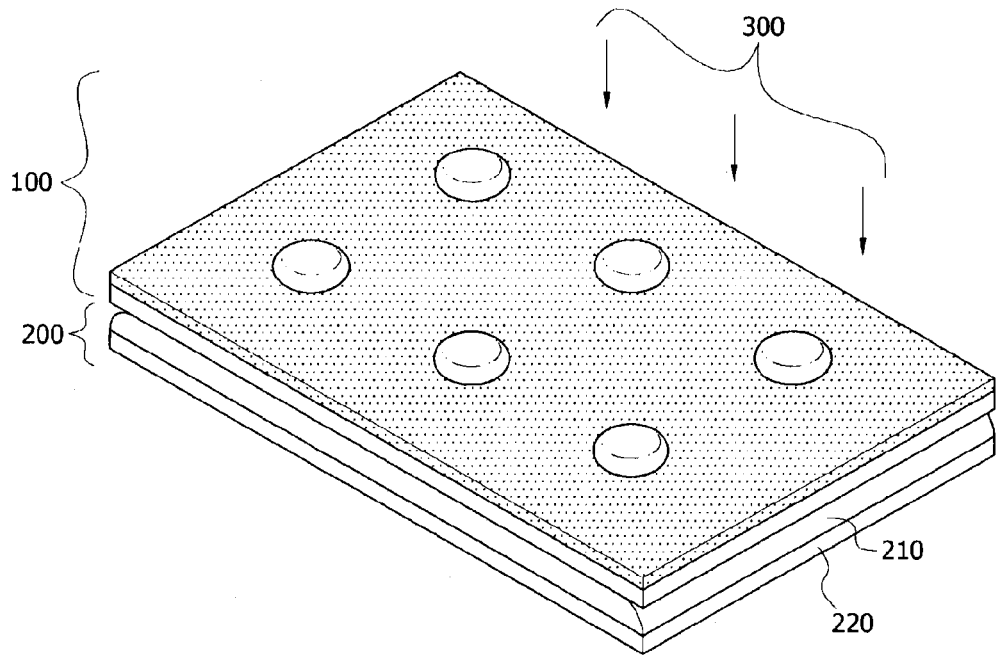
FIG. 3 is a diagram showing the structure of a biochip according to one embodiment of the present invention.

FIG. 3 shows the structure of a biochip according to one embodiment of the present invention, where a CMOS image sensor 200 is combined with the multilayer substrate 100 of FIG. 1. CMOS sensor lens 210, light diode 220 and light source 300 are showed.

Figure 4:
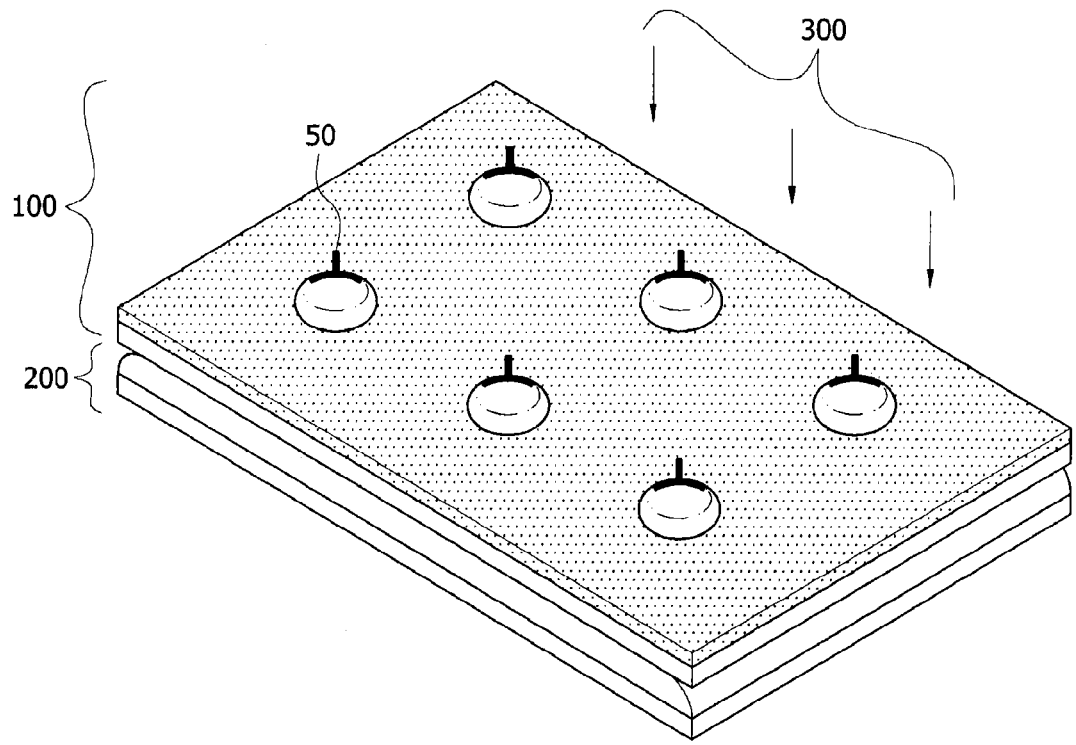
FIG. 4 is a diagram showing that a substance undergoing analysis binds to a dielectric layer of the biochip according to one embodiment of the present invention.

FIG. 4 shows that a substance undergoing analysis binds to the dielectric layer of the biochip according to the present invention.

When an analyte sample is put in contact with multilayer substrate 100, an analyte substance 50 specifically binds to a biological substance which is the dielectric layer 30 in a specific layer, causing a change in the intensity of light transmitted through the corresponding layer. The CMOS image sensor converts such a change in the intensity of light into an electrical signal, which is presented on a display, thereby allowing qualitative and quantitative analyses of the analyte substance contained in the sample. With a multilayer substrate greater than each image pixel, the individual layers binding to the analyte substance are compared with the control substrate not binding to the analyte substance in regard to the intensity of light to perform qualitative or quantitative analysis of the biological substance.

Hereinafter, for better understandings, the present invention will be described in further detail with reference to the following examples, which are only to exemplify the present invention and not intended to limit the scope of the present invention. Those examples of the present invention are provided to further completely describe the present invention to those skilled in the art.

Example 1

Fabrication of Biochip

Indium nanoparticles each having a different size were deposited in a different thickness on the surface of a glass substrate using indium beads (Sigma Aldrich) and a thermal evaporator (Daeki Hi-Tech). Various factors were controlled to prepare an indium nanoparticle layer having a desired thickness and a desired size. In this example, the evaporation was carried out under a gas pressure of 0.3 to 1 Pa, using an argon gas with the chamber exhaust pressure of $10^{-6}$ Torr, and the total gas pressure was acquired using a mass flow controller. The distance between the target and the substrate was maintained in the range of about 50 to 80 mm. The rate of the thermal evaporator was 0.05 to 0.1 Å/s. The thermal evaporator was stopped when a desired thickness was acquired.

The thickness of the metal nanoparticle layer was 5 nm, nm, 20 nm, and 40 nm, and the diameter of the metal nanoparticles was 30 to 50 nm, 70 to 100 nm, 150 to 200 nm, and 350 to 400 nm, respectively, depending on the thickness of the metal nanoparticle layer.

The CMOS image sensor was an 110,000-pixel single chip used for normal cellular phone camera. The CMOS image sensor was provided in the form of 10 bit ADC on chip (circuitry integrated on a semiconductor) with 376×314 pixels and supplied by Siliconfile Technologies Inc.

Example 2

Quantitative Analysis of Protein Depending on Change in Thickness of Metal Nanoparticle Layer As for the recombinant gamma-interferon used as a dielectric, a primary polyclonal gamma-interferon antibody (1° Ab) and a secondary antibody (FITC conjugated goat anti-globulin; 2° Ab) were supplied from Abcam. All the solutions and a buffer were prepared with distilled water. The buffer was PBS containing 138 mM NaCl and 2.7 mM KCl and having an acidity of pH 7.4. The gamma-interferon was diluted with 0.85% w/v NaCl solution to the final concentration of 5 µg/ml. The primary antibody was diluted with 1% BSA solution to the final concentrations of 1 µg/ml, 1 ng/ml, 1 pg/ml, and 1 fg/ml. The secondary antibody was diluted to the final concentration of 20 µg/ml in the same manner as the primary antibody.

The backlighting brightness of the CMOS image sensor was adjusted to the maximum level by manually controlling the integration time and the analogue value. With the maximum intensity of light calibrated, light was applied sequentially to the multilayer substrate where antigen-antibody binding occurred, to measure the number of photons.

Each of the substrates coated with indium nanoparticles in thickness of 5 nm, 10 nm, 20 nm, and 40 nm as prepared in Example 1 was cut into four pieces (5 mm×5 mm) (sixteen pieces in all) and washed with distilled water. All the substrates were exposed to the lens of the CMOS image sensor in order to calculate the input and output numbers of photons.

The sixteen substrates washed out were immersed in gamma-interferon antigen (5 μg/ml in concentration) and incubated at the room temperature for 60 minutes. Subsequently, the substrates were washed with distilled water and dried. After adsorption of antigens, all the sixteen substrates were exposed to the CMOS image sensor to analyze the number of photons.

Each time, one of the substrates having a specific thickness was put in a Petri dish containing primary antibodies each having a concentration of 1 μg/ml, 1 ng/ml, 1 pg/ml, or 1 fg/ml and temporarily shaken for 3-hour reaction. All the substrates were washed with distilled water to isolate the primary antibodies not adsorbed by the substrate and then dried out with an air compressor. The substrates with the primary antibodies stuck on were all immersed in a secondary antibody having a concentration of 20 μg/ml and cultivated for one hour in the shade. Subsequently, the substrates were washed with distilled water and then dried out to perform a photon analysis pertaining to the binding of the secondary antibodies. Each substrate was then exposed to the CMOS image sensor for analysis.

Figure 5:
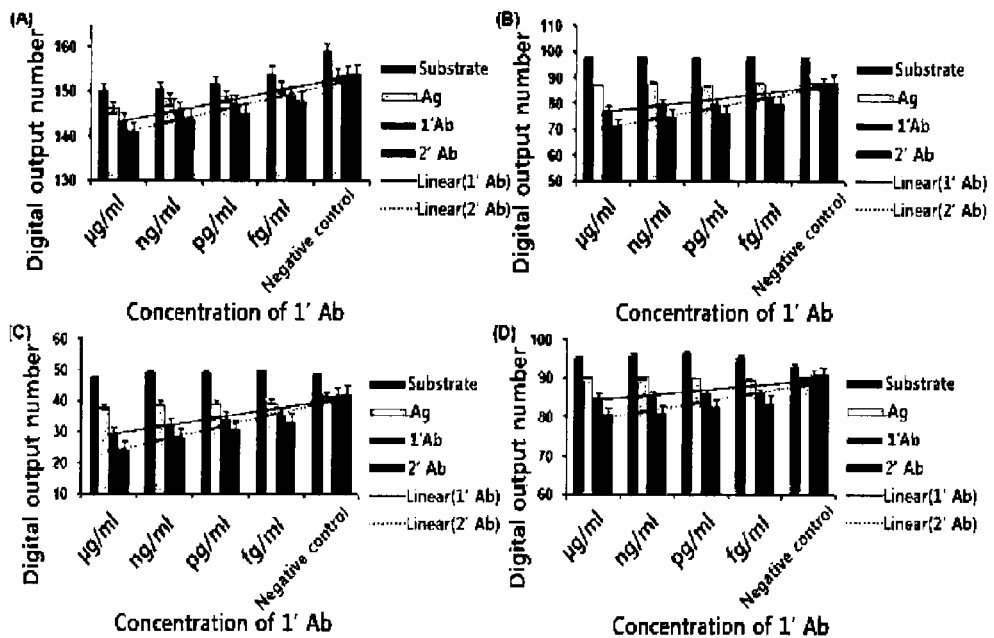
FIG. 5 is a graph showing the change in the number of photons caused by the binding of primary and secondary antibodies using a biochip according to another embodiment of the present invention in terms of a digital output number.

As shown in FIG. 5, the number of protons absorbed by the substrate with a coating of the indium nanoparticle layer as observed with a CMOS lens reduced as the antigens sequentially bind to the primary and secondary antibodies. The graphs (A), (B), (C) and (D) show the experimental results using the respective substrates each coated with an indium nanoparticle layer having a thickness of 5 nm, 10 nm, 20 nm, or 40 nm. The digital output number was drastically reduced as antigens (Ag) bind to the primary antibody (1 Ab) and the secondary antibody (2 Ab) on the substrates, as shown in the graphs (A), (B), (C) and (D). It is considered that the digital output number from the CMOS image sensor is in proportion to the number of photons detected by the CMOS image sensor. Such a decrease in the number of photons results from the progress of antigen-antibody binding, which blocks the photons from entering the CMOS image sensor to reduce the intensity of light absorbed from the CMOS lens.

It was revealed that the use of the biochip of the present invention enabled detection of antigen-antibody reaction to a femto-scale concentration of 1 fg/ml.

Example 3

Figure 6:
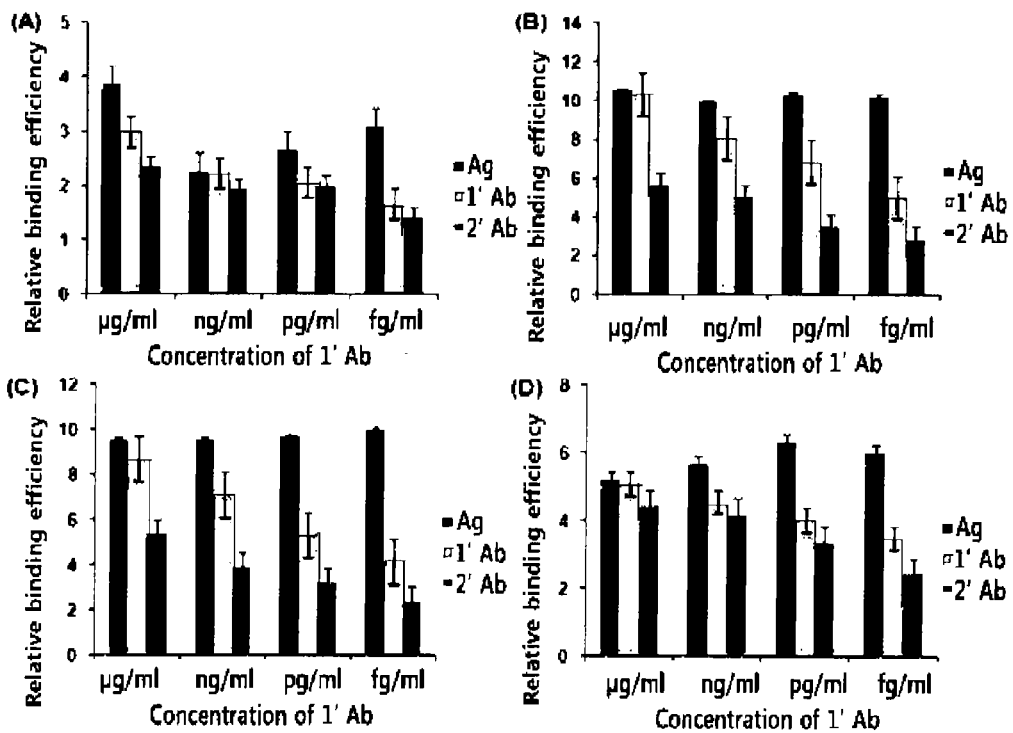
FIG. 6 is a graph showing the protein binding efficiency based on the results of FIG. 5.

Binding Efficiency of Protein Depending on Change in Thickness of Metal Nanoparticle Layer FIG. 6 is a graph showing the relative protein binding efficiency that the antigens and the primary and secondary antibodies bind to the indium nanoparticle layer having a thickness of 5 nm, 10 nm, 20 nm, or 40 nm. The relative binding efficiency of the antigens was determined by subtracting the digital output number upon the binding of indium nanoparticles and the antigens from the digital output number of the indium nanoparticle layer. The relative binding efficiency of the primary antibodies was determined by subtracting the digital output number upon the binding of indium nanoparticles, antigens and the primary antibodies from the digital output number during the binding of indium nanoparticles and the antigens. Likewise, the relative binding efficiency of the secondary antibodies was determined by subtracting the digital output number upon the binding of indium nanoparticles, antigens and the secondary antibodies from the digital output number during the binding of indium nanoparticles, antigens and the primary antibodies.

As can be seen from FIG. 6, the binding efficiency was drastically reduced with a decrease in the concentration of the primary antibodies. This agrees with the results that the decrement of the digital output number reduced with a decrease in the concentration of the primary antibodies in FIG. 5.

Furthermore, according to FIG. 6, the binding efficiency of the primary antibodies depends not only on the concentration of the primary antibodies but also on the degree of binding between the antigens and the metal nanoparticle layer.

Theoretically, the quantity of antigens or metal nanoparticles binding together must be constant, because the concentration of antigens was constant in all the experiments. However, the binding efficiency of antigens was around 10 for the indium nanoparticle layer having a thickness of 10 nm or 20 nm and remarkably reduced to about 3 or 6 for the indium nanoparticle layer having a thickness of 5 nm or 40 nm. The binding efficiency between the antigens and the metal nanoparticle layer affected the biding efficiency of primary and secondary antibodies.

Figure 7:
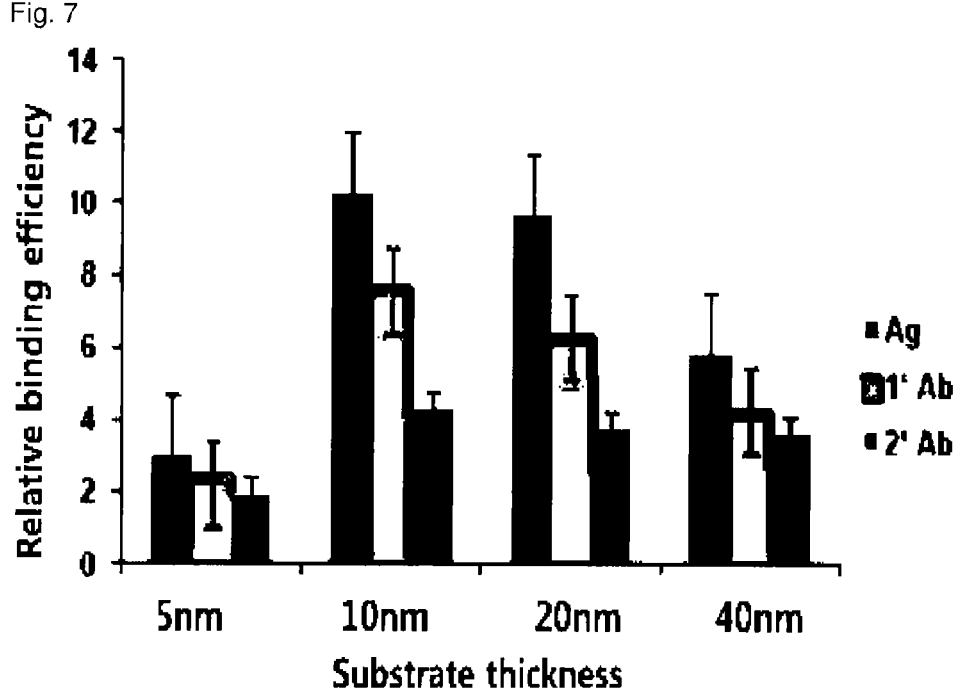
FIG. 7 is a graph showing the protein binding efficiency depending on the thickness of an indium nanoparticle layer based on the results of FIG. 6.

FIG. 7 is a graph showing the binding efficiency between protein and an indium nanoparticle layer having a defined thickness irrespective of the concentration of the primary antibodies in order to determine the optimal conditions for the binding efficiency with gamma-interferon antigens. The results of FIG. 7 are obtained as the averaged binding efficiency of FIG. 6 based on the thickness of the indium nanoparticle layer. The binding efficiency was as high as 10 to 12 for the indium nanoparticle layer having a thickness of 10 nm or 20 nm, but reduced to about 3 to 6 for the indium nanoparticle layer having a thickness of 5 nm or 40 nm. The reason of this phenomenon lies in that the size of the gamma-interferon protein is optimized when the indium nanoparticle layer (7 to 100 nm or 15 to 200 nm in particle diameter) has a thickness of 10 nm or 20 nm.

In conclusion, the affinity between the indium nanoparticle layer and the antigens depends on the diameter of the indium nanoparticles and the thickness of the indium nanoparticle layer. Considering this fact, the diameter of the indium nanoparticles for the indium nanoparticle layer having a thickness of 10 nm or 20 nm is suitable for binding to the gamma-interferon antigens and thus provides, thus providing a high binding efficiency with the primary antibodies relative to the diameter of the indium nanoparticles for the indium nanoparticle layer having a thickness of 5 nm or 40 nm.

Accordingly, the results of Examples 2 and 3 show that the biochip of the present invention is capable of detecting the antigen-antibody interaction in a wide concentration range, with high sensitivity for detecting a concentration up to 1 fg/ml. In addition, the biochip can detect the antigen-antibody interaction with highest sensitivity when the metal nanoparticle layer formed on the substrate has a thickness of about 10 to 20 nm.

Example 4

Morphological Analysis 4-1: FE-SEM Analysis

When protein binds to the surface of the indium nanoparticle layer, various phenomena are expected to occur on the nanometer-scale surface. To verify this, a field emission scanning electron microscope (FE-SEM; JEOL-ISM-7500F) was used to take an observation before and after treatment of the indium nanoparticle layer with protein.

Figure 8:
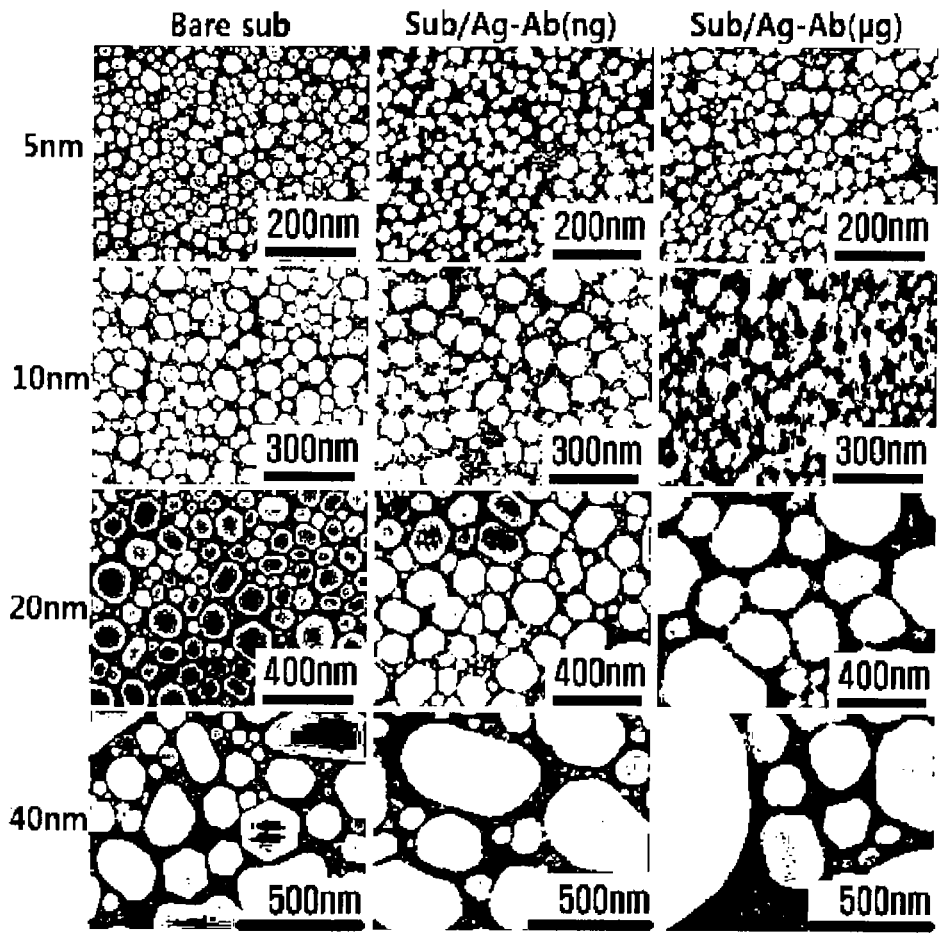
FIG. 8 is a FE-SEM picture showing the surface of the multilayer substrate before and after antibody treatment.

As shown in FIG. 8, the metal nanoparticle layer (Bare sub) prior to treatment with antigens mostly contained uniform particles. But, the metal nanoparticles bound together to form large particles when treated with primary antibodies having a nanogram-scale concentration (ng/ml; Sub/Ag-Ab(ng)) or a microgram-scale concentration (μg/ml; Sub/Ag-Ab(μg)) after treatment with antigens. This revealed that the metal nanoparticle layer having a uniform and smooth surface turned to have a rough surface due to the antigen-antibody interaction. In particular, such a change occurred most greatly when the metal nanoparticle layer was 10 nm or 20 nm thick, which agreed with the experimental results acquired using a CMOS image sensor.

4-2: AFM Analysis

A bio-atomic force microscope (AFM; Nanowizard II, JPK Instrument) was used to observe the surface roughness of the indium nanoparticle layer when protein is adsorbed by the indium nanoparticle layer (Analyzing a 2 μm×2 μm area of the substrate).

Figure 9:
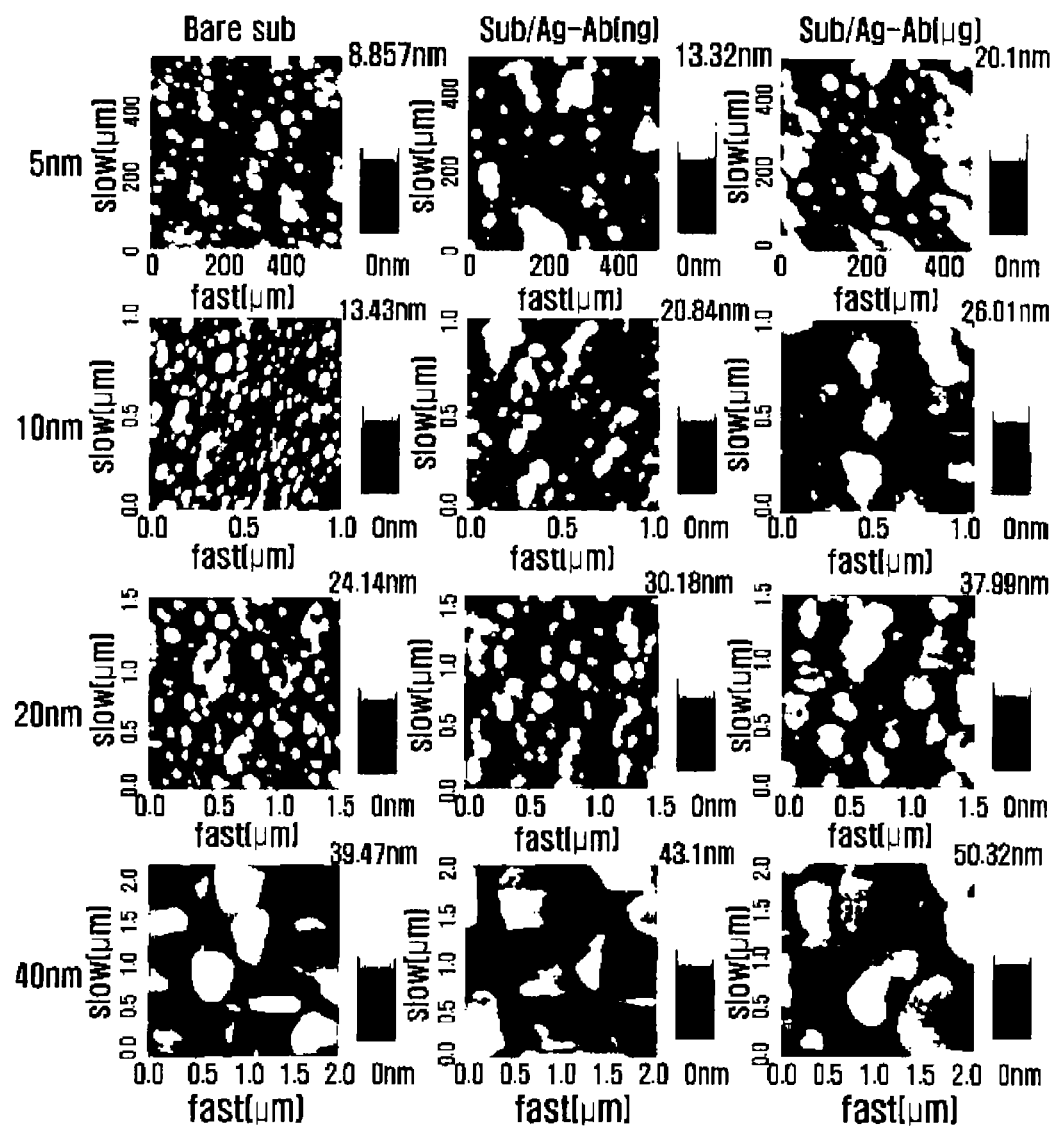
FIG. 9 is an AFM picture showing the surface of the multilayer substrate before and after antibody treatment.

As shown in FIG. 9, the metal nanoparticle layer (Bare sub) prior to treatment with antigens mostly contained uniform particles. But, the metal nanoparticles bound together to form large particles when treated with primary antibodies having a nanogram-scale concentration (ng/ml; Sub/Ag-Ab(ng)) or a microgram-scale concentration (μg/ml; Sub/Ag-Ab(μg)) after treatment with antigens. In particular, the metal nanoparticle layer had such a change most greatly when the metal nanoparticle layer was 10 nm or 20 nm in thickness, which agreed with the experimental results of Example 4-1.

4-3: RMS Measurement

The surface roughness (RMS) of the indium nanoparticle layer after addition of primary and secondary antibodies was measured.

As shown in Table 1, the roughness increased in ascending order of antigens, primary antibodies, and secondary antibodies, and the roughness difference pertaining to antigen-antibody interactions was definitely noticeable in the indium nanoparticle layer having a thickness of 10 nm or 20 nm.

TABLE 1

| | Roughness RMS Rq (nm) Thickness of InNP Substrate | | | |
|---|---|---|---|---|
| | 5 nm | 10 nm | 20 nm | 40 nm |
| InNP | 2.74 | 4.25 | 8.13 | 18.96 |
| InNP/Ag | 2.91 | 5.2 | 9.08 | 19.2 |
| InNP/Ag/1° Ab | | | | |
| μg/ml | 3.52 | 7.09 | 11.72 | 19.91 |
| ng/ml | 3.25 | 6.82 | 10.58 | 19.72 |
| pg/ml | 3.11 | 6.19 | 10.09 | 19.53 |
| fg/ml | 2.98 | 5.43 | 9.59 | 19.4 |
| InNP/Ag/2° Ab | | | | |

TABLE 1-continued

| | Roughness RMS Rq (nm) Thickness of InNP Substrate | | | |
|---|---|---|---|---|
| | 5 nm | 10 nm | 20 nm | 40 nm |
| μg/ml | 3.6 | 7.57 | 12.17 | 20.23 |
| ng/ml | 3.34 | 6.98 | 11.15 | 19.96 |
| pg/ml | 3.26 | 6.49 | 10.86 | 19.68 |
| fg/ml | 3.21 | 6.16 | 10.16 | 19.57 |

Comparative Example 1

Fluorescence Microscopic Analysis

The indium nanoparticle-antigen substrate treated with a primary antibody (gamma-interferon) and a secondary antibody (FITC-conjugated goat anti-globulin) was measured in regard to the fluorescence strength using a fluorescence microscope.

Figure 10:
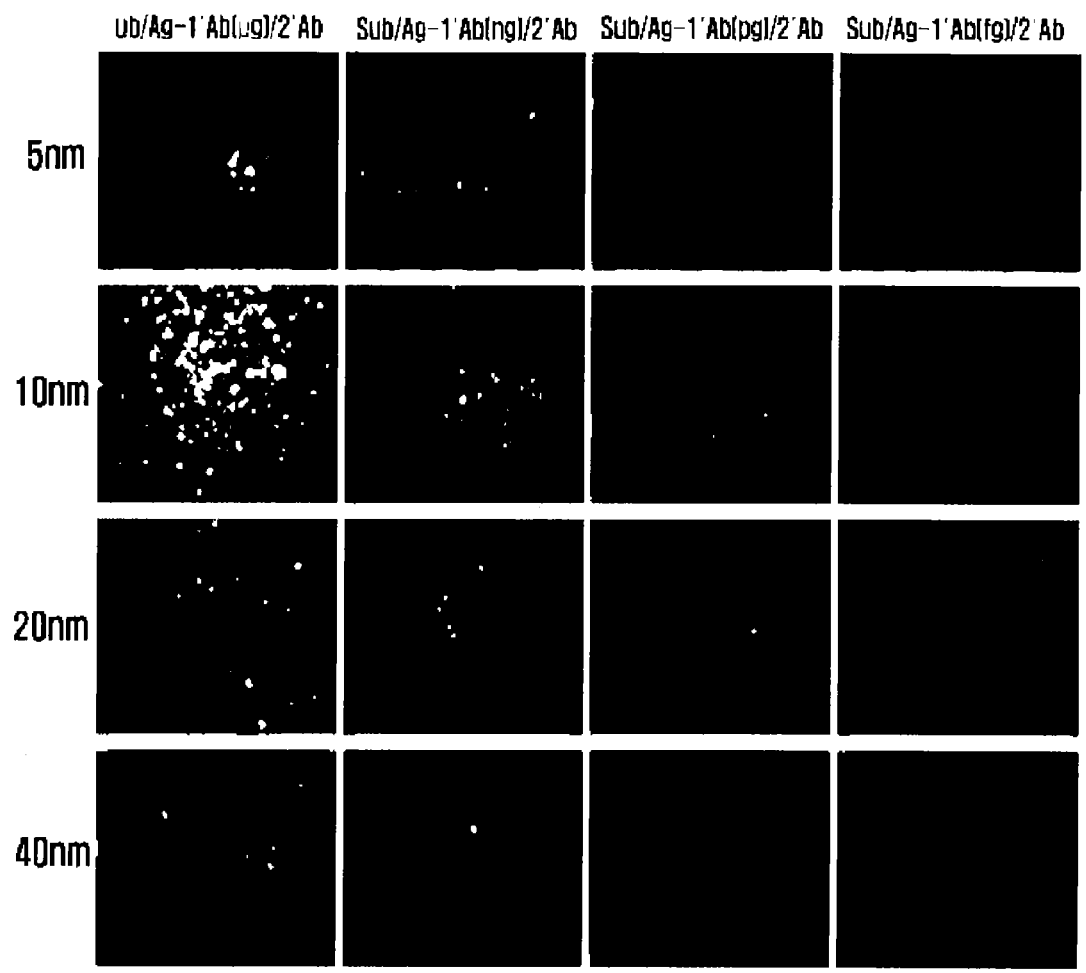
FIG. 10 is a fluorescence microscopic picture showing an antigen-antibody reaction.

As shown in FIG. 10, the fluorescence strength decreased with a decrease in the concentration of the primary antibody. Little fluorescence was detected when the concentration of the primary antibody was on a pg/ml scale, and no fluorescence was detected when the concentration of the primary antibody was on a fg/ml scale.

What is claimed is:

1. A biochip comprising:
a multilayer comprising a substrate, an indium nanoparticle layer deposited on the substrate, a dielectric layer deposited on the indium nanoparticle layer in the substrate, and a charging layer deposited on a portion of the indium nanoparticle layer deprived of the dielectric layer; and
a CMOS image sensor;
wherein the indium nanoparticle layer is 10 to 20 nm in thickness; and
wherein the dielectric layer is configured to cause an analyte without a tag to bind to the dielectric layer, and in response to the bound analyte without a tag the CMOS image sensor can measure a change in light intensity and provide a signal representative of detected analyte without a tag.

2. The biochip according to claim 1, wherein the dielectric layer comprises a biological substance selected from the group consisting of DNA, RNA, protein, enzyme, antigen, antibody, peptide, carbohydrate, and liquid.

3. The biochip according to claim 1, wherein the charging layer comprises a metalloprotein.

4. The biochip according to claim 3, wherein the metalloprotein is aldolase.

* * * * *